(12) United States Patent
Sagripanti et al.

(10) Patent No.: US 8,017,330 B1
(45) Date of Patent: Sep. 13, 2011

(54) ARTIFICIAL CHIMERAS ENGINEERED TO SIMULATE MULTIPLE BIOLOGICAL THREAT AGENTS

(75) Inventors: Jose-Luis Sagripanti, Bel Air, MD (US); Monica Carrera, Buenos Aires (AR)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 12/873,777

(22) Filed: Sep. 1, 2010

Related U.S. Application Data

(62) Division of application No. 12/177,527, filed on Jul. 22, 2008, now Pat. No. 7,790,452.

(51) Int. Cl.
  *C12Q 1/68*  (2006.01)

(52) U.S. Cl. .......................................................... 435/6
(58) Field of Classification Search .................. None
  See application file for complete search history.

(56) References Cited

OTHER PUBLICATIONS

Carrera et al (Conference proceeding, NTIS Accession No. ADA481840, Edgewood Chemical Biological Center, Aberdeen Proving Ground, MD, USDGRDR0820, Nov. 1, 2006 pp. 1-9).*

* cited by examiner

*Primary Examiner* — Patricia A Duffy
(74) *Attorney, Agent, or Firm* — Ulysses John Biffoni

(57) ABSTRACT

This invention provides safe, non-infectious chimeras that include the nucleic acid signature of most bacterial and viral biological threat agents. These chimeras mimic properties of threat agents and are useful as simulants to develop, evaluate, test, and train on nucleic acid-based biodetectors and diagnostic products of interest in biodefense, without the need for accessing or producing virulent agents.

3 Claims, 6 Drawing Sheets

```
        ┌──────────────┐
        │      R       │       ┌─────────────────────┐
┌───────┤  (Brucella   │       │       ALL-G         │
│   G   │  melitensis  │──────▶│  THREAT AGENTS      │
│(Brucella│  3198 genes)│      │ DATABASE EXCEPT "G" │
│ group) │              │      │  (excluding Brucella)│
└────────┘──────────────┘      └──────────┬──────────┘
                                          │
                                          ▼
                               ┌─────────────────────┐
                               │ BLAST (R) VERSUS (ALL-G)│
                               └──────────┬──────────┘
   ┌────────────────┐                     ▼
   │ DESCARTED GENES│           ◇ FIRST ◇
   │  (639 GENES)   │◀──────────  SELECTION
   └────────────────┘                     │
                                          ▼
                               ┌─────────────────────┐
                               │ GENES WITH NO HITS (NO)│
                               │     (2559 GENES)    │
                               └──────────┬──────────┘
   ┌────────────────┐                     ▼
   │   G DATABASE   │           ┌─────────────────────┐
   │     [G-R]      │──────────▶│ BLAST (NO) VERSUS (G-R)│
   └────────────────┘           └──────────┬──────────┘
   ┌────────────────┐                     ▼
   │  NOT CONSERVED │           ◇ SECOND ◇
   │ GENES DESCARTED│◀──────────  SELECTION
   └────────────────┘                     │
                                          ▼
                               ┌─────────────────────┐
                               │  CONSERVED GENES    │
                               │     SELECTED        │
                               │    (2151 GENES)     │
                               └──────────┬──────────┘
                                          │
                               ┌──────────▼──────────┐
                               │ LIST OF SELECTED    │
                               │ GENES FOR EVERY     │
                               │  THREAT AGENT       │
                               └─────────────────────┘
```

FIG.1

| Order in the chimerical DNA | Organism or group | Preferred size in sample | Size in Simulant | Digested with EcoR1 | Digested with SmaI |
|---|---|---|---|---|---|
| 1 | Francisella tularensis | 230 | 100 | 37 / 63 | 29 / 71 |
| 3 | Burkholderia group | 260 | 115 | 37 / 78 | 29 / 86 |
| 5 | Rickettsia group | 290 | 130 | 37 / 93 | 29 / 101 |
| 7 | Coxiella burnetti | 310 | 145 | 76 / 69 | 68 / 77 |
| 9 | Brucella group | 330 | 160 | 77 / 85 | 75 / 85 |
| 10 | Escherichia coli O157:H7 group | 350 | 175 | 91 / 84 | 83 / 92 |
| 8 | Variola virus | 380 | 190 | 129 / 61 | 121 / 69 |
| 6 | Bacillus anthracis pXO1 | 150 | 205 | 118 / 87 | 110 / 95 |
| 4 | Bacillus anthracis pXO2 | 169 | 220 | 130 / 90 | 122 / 98 |
| 2 | Yersinia group | 200 | 235 | 153 / 82 | 145 / 90 |

FIG. 2

| Order in the chimerical DNA | Virus | Size in pathogen | Size in Simulant | Digest with EcoR1 | Digested with SmaI |
|---|---|---|---|---|---|
| 1 | Lassa | 245 | 118 | 80 / 38 | 89 / 29 |
| 3 | Yellow Fever | 268 | 128 | 40 / 38 | 49 / 29 |
| 5 | Ebola Zaire | 304 | 149 | 111 / 38 | 120 / 29 |
| 7 | EEEV | 321 | 160 | 102 / 58 | 111 / 49 |
| 9 | Junin | 355 | 180 | 118 / 62 | 127 / 53 |
| 11 | Marburg | 376 | 190 | 118 / 72 | 127 / 63 |
| 13 | Dengue | 511 | 210 | 121 / 89 | 130 / 80 |
| 12 | Crimean Congo | 549 | 220 | 116 / 104 | 125 / 95 |
| 10 | VEEV | 108 | 232 | 111 / 121 | 120 / 112 |
| 8 | Influenza | 138 | 256 | 124 / 132 | 133 / 123 |
| 6 | RVFV | 170 | 280 | 135 / 145 | 144 / 136 |
| 4 | Machupo | 200 | 292 | 141 / 151 | 150 / 142 |
| 2 | Actin (+) | 450 | 450 | 221 / 229 | 230 / 220 |

SEQUENCE LISTING

<160> NUMBER OF SEQ ID NOS: 28

<210> SEQ ID NO 1
<211> LENGTH: 135
<212> TYPE: DNA
<213> ORGANISM: Francisella tularensis

<400> SEQUENCE: 1

```
ggatccgaca agcttatggc tttgcagcca cttttgcaat cgctgtgtga gcccgggcag      60
cgaattccca tttagatttt tttgaatatg cttgtaaaga ccgaggctca gaactaatcg     120
cagctacagc acaag                                                      135
```

<210> SEQ ID NO 2
<211> LENGTH: 270
<212> TYPE: DNA
<213> ORGANISM: Yersinia pestis

<400> SEQUENCE: 2

```
ggatcctgaa agcttgctgg ggcgaaccca cctcattggc tatggcggcg tcgcctgtca      60
cgtcctgttt gagtgggata acgccacga tgagttcgat ctcgccatac tggagaaagc     120
atggaaccag ctcatcgcac gccacgatat gttgcgtatg gtggttgccc ggggcctgaa     180
ttctgacgat cctcattatg tcaatatcgg tacggtgtta gacaacgccg actgacgccg     240
gagtatcaca tcccgcgtga cgatctgcgc                                      270
```

<210> SEQ ID NO 3
<211> LENGTH: 150
<212> TYPE: DNA
<213> ORGANISM: Burkholderia mallei

<400> SEQUENCE: 3

```
ggatccatga agcttcattc gtcttttgcca ttgccctgtc atttgccgca gcccgggtgc      60
tgaattcgtc agcaatgcga aatttacatc cctacgcgag ccttttgttt ttaccgacct     120
gagtctgttc agtcagttgt tctcgcaccc                                      150
```

<210> SEQ ID NO 4
<211> LENGTH: 255
<212> TYPE: DNA
<213> ORGANISM: Bacillus anthracis

<400> SEQUENCE: 4

```
ggatccctca agcttttaca cgttttgctg accaatctaa gcctgcgttc ttcgtaaatg      60
gttttgcagc gaatgatccc tcatcaacat tacgtatttg gaacgtgtg gatgattttg     120 gatatagtaa tctagctcca attgcccggg agatgaattc tacatctgcg cgaatgatat     180
attggtttac tgacgaggag caaccgatta agcgccgtag cgttgatcgt actgagcagt     240
ttgctaggga tgttt                                                      255
```

<210> SEQ ID NO 5
<211> LENGTH: 165
<212> TYPE: DNA
<213> ORGANISM: Rickettsia sp.

<400> SEQUENCE: 5

```
ggatccggaa agcttagctg gtatcgctta ttttagaggt tatagagttc gcccgggtag      60
tgaattcgta aacctttatt ttttgatctt aatatttcta ctagaaccca aaacgtatcc     120
```

```
caagttcaaa gagctttact tttacctcaa gaagtaatac agtta              165
```

<210> SEQ ID NO 6
<211> LENGTH: 240
<212> TYPE: DNA
<213> ORGANISM: Bacillus anthracis

<400> SEQUENCE: 6

```
ggatcctcta agcttgaaaa aggattggat ttcaagttgt actggaccga ttctcaaaat    60
aaaaagaag tgatttctag tgataactta caattgccag aattaaaaca aaaatcttcg   120
aactcaagaa aacccgggga aagaattctc atctcctgaa aaatggagca cggcttctga   180
tccgtacagt gatttcgaaa aggttggacc tacggttcca gaccgtgaca atgatggaat   240
```

<210> SEQ ID NO 7
<211> LENGTH: 180
<212> TYPE: DNA
<213> ORGANISM: Coxiella burnetii

<400> SEQUENCE: 7

```
ggatccacta agcttcggat tgttacccaa cgaaaccttg cgtgaggcat tgaatcggga    60
attagatgaa gaagtgggac tgagtcctca cccgggtaca gaattccaat ggcggtgggt   120
tgattattgg tatccggtgg accacgtcgt tgagtttaag cgagacgttt atcagaaagt   180
```

<210> SEQ ID NO 8
<211> LENGTH: 225
<212> TYPE: DNA
<213> ORGANISM: Variola virus

<400> SEQUENCE: 8

```
ggatccataa agcttcggaa gagatgcagc accgtataca ccacccaatg gaatcattag    60
tatactctac accttatcct cagacacaga tatctaaaaa aataggtgat gatgcaactc   120
tatcatgtag tagaaataat atacccggga cgtgaattcc aaacaaaatg tggaatagga   180
tacggagtat ccggacacac gtctgttgga gacgtcatct gttct                  225
```

<210> SEQ ID NO 9
<211> LENGTH: 195
<212> TYPE: DNA
<213> ORGANISM: Brucella sp.

<400> SEQUENCE: 9

```
ggatcctaga agcttaattg tgggccgatg gcgtcatcca tgtgctgggt gtcgggctgg    60
cgcttgccgg tgccattgcc atgctgttct atttcctccc gggaatcgaa ttctatgggc   120
gaccgcgcgc tgcccctgct gctgttcgtg tggagcgtgg ctttcgtcgg catcatgctc   180
aaactgttca tgccg                                                   195
```

<210> SEQ ID NO 10
<211> LENGTH: 210
<212> TYPE: DNA
<213> ORGANISM: Escherichia coli

<400> SEQUENCE: 10

```
ggatccctga agcttgcgcg ctaacgcagg cctgaactca tcgtcggatg aattacaggc    60
ccagacgcgt attgccggaa tgcgctcaac gctggagcaa tatcacccgg ggcacgaatt   120
caagcgcaat actggccaac gctcagtatt caggggggta aaacgcgcta ccagaccagc   180
gaccgctcgt attgggatga tcagctacaa                                   210
```

```
<210> SEQ ID NO 11
<211> LENGTH: 90
<212> TYPE: DNA
<213> ORGANISM: Variola virus

<400> SEQUENCE: 11
tcattagtat actctacacc ttatcctcag acacagatat ctaaaaaaat aggtgatgat    60
gcaactctat catgtagtag aaataatata                                    90

<210> SEQ ID NO 12
<211> LENGTH: 2040
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
ggatccgaca agcttatggc tttgcagcca cttttgcaat cgctgtgtga gcccgggcag      60
cgaattccca tttagatttt tttgaatatg cttgtaaaga ccgaggctca gaactaatcg     120
cagctacagc acaagggatc ctgaaagctt gctggggcga acccacctca ttggctatgg    180
cggcgtcgcc tgtcacgtcc tgtttgagtg ggataaacgc cacgatgagt tcgatctcgc    240
catactggag aaagcatgga accagctcat cgcacgccac gatatgttgc gtatggtggt    300
tgcccggggc ctgaattctg acgatcctca ttatgtcaat atcggtacgg tgttagacaa    360
cgccgactga cgccggagta tcacatcccg cgtgacgatc tgcgcggatc catgaagctt    420
cattcgtctt tgccattgcc ctgtcatttg ccgcagcccg ggtgctgaat tcgtcagcaa    480
tgcgaaattt acatccctac gcgagccttt tgtttttacc gacctgagtc tgttcagtca    540
gttgttctcg caccccggatc cctcaagctt ttacacgttt tgctgaccaa tctaagcctg    600
cgttcttcgt aaatggtttt gcagcgaatg atccctcatc aacattacgt atttgggaac    660
gtgtggatga ttttggatat agtaatctag ctccaattgc ccgggagatg aattctacat    720
ctgcgcgaat gatatattgg tttactgacg aggagcaacc gattaagcgc cgtagcgttg    780
atcgtactga gcagtttgct agggatgttt ggatccggaa agcttagctg gtatcgctta    840
ttttagaggt tatagagttc gcccgggtag tgaattcgta aacctttatt ttttgatctt    900
aatatttcta ctagaaccca aaacgtatcc caagttcaaa gagctttact tttacctcaa    960
gaagtaatac agttaggatc ctctaagctt gaaaaaggat tggatttcaa gttgtactgg   1020
accgattctc aaaataaaaa agaagtgatt tctagtgata acttacaatt gccagaatta   1080
aaacaaaaat cttcgaactc aagaaaaccc ggggaaagaa ttctcatctc ctgaaaaatg   1140
gagcacggct tctgatccgt acagtgattt cgaaaaggtt ggacctacgg ttccagaccg   1200
tgacaatgat ggaatggatc cactaagctt cggattgtta cccaacgaaa ccttgcgtga   1260
ggcattgaat cgggaattag atgaagaagt gggactgagt cctcacccgg gtacagaatt   1320
ccaatggcgg tgggttgatt attggtatcc ggtggaccac gtcgttgagt ttaagcgaga   1380
cgtttatcag aaagtggatc cataaagctt cggaagagat gcagcaccgt atacaccacc   1440
caatggaatc attagtatac tctacacctt atcctcagac acagatatct aaaaaaatag   1500
gtgatgatgc aactctatca tgtagtagaa ataatatacc cggacgtgaa ttccaaaca   1560 aaatgtggaa taggatacgg agtatccgga cacacgtctg ttggagacgt catctgttct   1620
ggatcctaga agcttaattg tgggccgatg gcgtcatcca tgtgctgggt gtcgggctgg   1680
cgcttgccgg tgccattgcc atgctgttct atttcctccc gggaatcgaa ttctatgggc   1740
```

```
gaccgcgcgc tgcccctgct gctgttcgtg tggagcgtgg ctttcgtcgg catcatgctc    1800
aaactgttca tgccgggatc cctgaagctt gcgcgctaac gcaggcctga actcatcgtc    1860
ggatgaatta caggcccaga cgcgtattgc cggaatgcgc tcaacgctgg agcaatatca    1920
cccggggcac gaattcaagc gcaatactgg ccaacgctca gtattcaggg gggtaaaacg    1980
cgctaccaga ccagcgaccg ctcgtattgg gatgatcagc tacaaaagct tagaggatcc    2040

<210> SEQ ID NO 13
<211> LENGTH: 168
<212> TYPE: DNA
<213> ORGANISM: Zaire ebolavirus

<400> SEQUENCE: 13
aagcttcgcg gatcccggca attgcactcg gagtcgccac agcacacggg agtaccctcg     60
caggagtaaa tgttggagaa cagtatcaac aactcagaga ggctgccact gaggctgaga    120
agcaagaatt ctaccccggg tgctgcgtca ctgcccaaaa caagtgga                 168

<210> SEQ ID NO 14
<211> LENGTH: 179
<212> TYPE: DNA
<213> ORGANISM: Eastern equine encephalitis virus

<400> SEQUENCE: 14
aagcttcgcg gatcctttac ttgtctgcgg cgccttgggc gccgtagtcg aacgcccagg     60
ttatgcaccc gttcacctac agatacagct ggttaatacc aggataattc catcaagaat    120
tctaccccgg gacaggtgtt tacccattca tgtggggagg agcctactgc ttctgcgac     179

<210> SEQ ID NO 15
<211> LENGTH: 199
<212> TYPE: DNA
<213> ORGANISM: Junin virus

<400> SEQUENCE: 15
aagcttcgcg gatccgcacc tctgatccag acatgcagtc gacccttaac tttgacatca     60
aatccacatg atggatttga tttgcatatg ccatcaagaa atatcttaga ccttgtaaaa    120
atgtctggtt ccgaattcta ccccgggccc attgatggat agatagatag aatagcacct    180
tgacttctca cctgttttt                                                 199

<210> SEQ ID NO 16
<211> LENGTH: 209
<212> TYPE: DNA
<213> ORGANISM: Marburg virus

<400> SEQUENCE: 16
aagcttcgcg gatccatgaa gttgctagtt tcaagcaggc gttgagcaac ctagcccgac     60
atggagaata cgcaccgttc gcacgggttc tgaatttatc agggattaac aacctcgaac    120
atggactcta tcgaattcta ccccgggttc agaaaactga atcacacac agtcagacac     180 tagccgtcct cagccagaaa cgagaaaaa                                      209

<210> SEQ ID NO 17
<211> LENGTH: 229
<212> TYPE: DNA
<213> ORGANISM: Dengue virus type 1

<400> SEQUENCE: 17
aagcttcgcg gatcctttca atatgctgaa acgcgagaga aaccgcgtgt caactgtttc     60
```

-continued

```
acagttggcg aagagattct caaaaggatt gctttcaggc caaggaccca tgaaattggt    120
gatggctttt atagcgaatt ctaccccggg ttatgtgagg acacaatgac ctacaaatgc    180
ccccggatca ctgagacgga acctgaagac attgactgtt ggtgcaatg               229
```

<210> SEQ ID NO 18
<211> LENGTH: 251
<212> TYPE: DNA
<213> ORGANISM: Venezuelan equine encephalitis virus

<400> SEQUENCE: 18

```
aagcttcgcg gatcctagtt agttgcgacg ggtacgtcgt taaaagaata gctatcagtc    60
caggcctgta tgggaagcct tcaggctatg ctgctacgat gcaccgttaa agaatagct    120 atcaggaatt ctaccccggg ggctatgctg ctacgatgca ccgttaaaag aatagctatc   180
agtccaggcc tgtatgggaa gccttcaggc tatgctgcta cgatgcaccg cgagggattc    240
ttgtgctgca a                                                         251
```

<210> SEQ ID NO 19
<211> LENGTH: 239
<212> TYPE: DNA
<213> ORGANISM: Crimean-Congo hemorrhagic fever virus

<400> SEQUENCE: 19

```
aagcttcgcg gatccaattg atgatgagca tgtcaggcat tgattgtata aatatccca    60 cagggcagct tatcacccat ggaagagtga gtgcaaaaca taacgatggg aacctgaaag    120
atagaagcga gaattctacc ccgggaacct gtgcccttc aggttgactg tatattgttc     180
aaagaagtgg cagctgaatg catgaagagg tacattggca caccttatga gggaattgt    239
```

<210> SEQ ID NO 20
<211> LENGTH: 275
<212> TYPE: DNA
<213> ORGANISM: Influenza virus A

<400> SEQUENCE: 20

```
aagcttcgcg gatccaaacc atttgaatgg atgtcaatcc gactctactg ttcctaaagg    60
ttccagcgca aaatgccata agcaccacat tcccttatac tggagatcct ccatacagcc    120
atggaacagt ctactgttga attctacccc gggtggaaca gtctactgtt cctaaaggtt   180
ccagcgcaaa atgccataag caccacattc ccttatactg agatcctcc atacagccat     240 ggaacaggaa caggatacac catggacaca gtcaa                              275
```

<210> SEQ ID NO 21
<211> LENGTH: 299
<212> TYPE: DNA
<213> ORGANISM: Rift valley fever virus

<400> SEQUENCE: 21

```
aagcttcgcg gatccttatg agtgcactgc tcagtacgcc aatgcctatt gttcacatgc    60
taatgggtca gggattgtgc agatacaagt atcaggggtc tggaagaagc ctttatgtgt   120
agggtatgag agagtggttg tgaagagagg aattctaccc cgggacatgc taatgggtca   180
gggattgtgc agatacaagt atcaggggtc tggaagaagc ctttatgtgt agggtatgag   240
agagtggttg tgaagagaga actctctgcc aagcccatcc agagagttga gccttgcac    299
```

<210> SEQ ID NO 22
<211> LENGTH: 311

```
<212> TYPE: DNA
<213> ORGANISM: Machupo virus

<400> SEQUENCE: 22
aagcttcgcg gatccttcat tcatcatgtc taaagcaatg cagacatcca gaaattttag      60
cctcccgcta tccattgttc tgctgacctg aagatcatte ataaatggag tcaagtgttc    120
gtcaaaaaga actggataat ttctccttat agattgaatt ctaccccggg tctgctgacc    180
tgaagatcat tcataaatgg agtcaagtgt tcgtcaaaaa gaactggata atttctcctt    240
atagattgca gaacatggtt cattcccagt tggtcttcaa tttgtctcac cactttaggc    300
ttcacagccc a                                                        311

<210> SEQ ID NO 23
<211> LENGTH: 137
<212> TYPE: DNA
<213> ORGANISM: Lassa virus

<400> SEQUENCE: 23
aagcttcgcg gatccttatc ctgggtgacc acttcatttt ggttgatgct aagtcgctca     60
taaatggcag tatgtgtttt tcaaatacag atgggaattc taccccggga agacccatgc    120
acccagttct attgcag                                                  137

<210> SEQ ID NO 24
<211> LENGTH: 147
<212> TYPE: DNA
<213> ORGANISM: Yellow fever virus

<400> SEQUENCE: 24
aagcttcgcg gatcctgcta agctgtgagg cagtgcaggc tgggacagcc gacctccagg     60
ttgcgaaaaa cctggtttct gggacctccc accccagagt aaaagaattc taccccgggc    120
agtttgctca agaataagca gaccttt                                       147

<210> SEQ ID NO 25
<211> LENGTH: 485
<212> TYPE: DNA
<213> ORGANISM: Homo sapiens

<400> SEQUENCE: 25
aagcttcgcg gatccgcgtc cgccccgcga gcacagagcc tcgcctttgc cgatccgccg     60
cccgtccaca cccgccgcca gctcaccatg gatgatgata tcgccgcgct cgtcgtcgac    120
aacggctccg gcatgtgcaa ggccggcttc gcgggcgacg atgccccccg gccgtcttc    180
ccctccatcg tggggcgccc caggcaccag ggcgtgatgg tgggcatggg tcagaaggat    240
tccgaattct accccgggta tgtgggcgac gaggcccaga gcaagagagg catcctcacc    300
ctgaagtacc ccatcgagca cggcatcgtc accaactggg acgacatgga gaaaatctgg    360
caccacacct tctacaatga gctgcgtgtg gctcccgagg agcaccccgt gctgctgacc    420
gaggcccccc tgaaccccaa ggccaaccgc gagaagatga cccagatcat gtttgagacc    480
ttcaa                                                               485

<210> SEQ ID NO 26
<211> LENGTH: 3143
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 26

```
aagcttcgcg gatccttatc ctgggtgacc acttcatttt ggttgatgct aagtcgctca      60
taaatggcag tatgtgtttt tcaaatacag atgggaattc taccccggga agacccatgc     120
acccagttct attgcagaag cttcgcggat ccgcgtccgc cccgcgagca cagagcctcg     180
cctttgccga tccgccgccc gtccacaccc gccgccagct caccatggat gatgatatcg     240
ccgcgctcgt cgtcgacaac ggctccggca tgtgcaaggc cggcttcgcg ggcgacgatg     300
cccccgggc cgtcttcccc tccatcgtgg ggcgcccag gcaccagggc gtgatggtgg       360
gcatgggtca gaaggattcc gaattctacc ccgggtatgt gggcgacgag cccagagca     420
agagaggcat cctcaccctg aagtaccccca tcgagcacgg catcgtcacc aactgggacg     480
acatggagaa aatctggcac acaccttct acaatgagct gcgtgtggct cccgaggagc     540
accccgtgct gctgaccgag gccccctga accccaaggc caaccgcgag aagatgaccc     600
agatcatgtt tgagaccttc aaaagcttcg cggatcctgc taagctgtga ggcagtgcag     660
gctgggacag ccgacctcca ggttgcgaaa acctggtttt ctgggacctc ccaccccaga     720
gtaaaagaat tctaccccgg gcagtttgct caagaataag cagacccttta agcttcgcgg     780
atccttcatt catcatgtct aaagcaatgc agacatccag aaattttagc ctcccgctat     840
ccattgttct gctgacctga agatcattca taaatggagt caagtgttcg tcaaaaagaa     900
ctggataatt tctccttata gattgaattc taccccgggt ctgctgacct gaagatcatt     960
cataaatgga gtcaagtgtt cgtcaaaaag aactggataa tttctcccta tagattgcag    1020
aacatggttc attcccagtt ggtcttcaat ttgtctcacc actttaggct tcacagccca    1080
aagcttcgcg gatcccggca attgcactcg gagtcgccac agcacacggg agtaccctcg    1140
caggagtaaa tgttggagaa cagtatcaac aactcagaga ggctgccact gaggctgaga    1200
agcaagaatt ctaccccggg tgctgcgtca ctgcccaaaa caagtggaaa gcttcgcgga    1260
tccttatgag tgcactgctc agtacgccaa tgcctattgt tcacatgcta atgggtcagg    1320
gattgtgcag atacaagtat caggggtctg gaagaagcct ttatgtgtag ggtatgagag    1380
agtggttgtg aagagaggaa ttctaccccg ggacatgcta atgggtcagg gattgtgcag    1440
atacaagtat caggggtctg gaagaagcct ttatgtgtag ggtatgagag agtggttgtg    1500
aagagagaac tctctgccaa gcccatccag agagttgagc cttgcacaag cttcgcggat    1560
ccttttacttg tctgcggcgc cttgggcgcc gtagtcgaac gcccaggtta tgcacccgtt    1620
cacctacaga tacagctggt taataccagg ataattccat caagaattct accccgggac    1680
aggtgtttac ccattcatgt ggggaggagc ctactgcttc tgcgacaagc ttcgcggatc    1740
caaaccattt gaatggatgt caatccgact ctactgttcc taaaggttcc agcgcaaaat    1800
gccataagca ccacattccc ttatactgga gatcctccat acagccatgg aacagtctac    1860
tgttgaattc taccccgggt ggaacagtct actgttccta aaggttccag cgcaaaatgc    1920
cataagcacc acattccctt atactggaga tcctccatac agccatggaa caggaacagg    1980
atacaccatg acacagtca aaagcttcgc ggatccgcac ctctgatcca gacatgcagt    2040
cgacccttaa ctttgacatc aaatccacat gatggatttg atttgcatat gccatcaaga    2100
aatatcttag accttgtaaa aatgtctggt tccgaattct accccgggcc cattgatgga    2160
tagatagata gaatagcacc ttgacttctc acctgttttt aagcttcgcg gatcctagtt    2220
agttgcgacg ggtacgtcgt taaaagaata gctatcagtc caggcctgta tgggaagcct    2280
tcaggctatg ctgctacgat gcaccgttaa aagaatagct atcaggaatt ctaccccggg    2340
```

-continued

```
ggctatgctg ctacgatgca ccgttaaaag aatagctatc agtccaggcc tgtatgggaa   2400
gccttcaggc tatgctgcta cgatgcaccg cgagggattc ttgtgctgca aaagcttcgc   2460
ggatccatga agttgctagt ttcaagcagg cgttgagcaa cctagcccga catggagaat   2520
acgcaccgtt cgcacgggtt ctgaatttat cagggattaa caacctcgaa catggactct   2580
atcgaattct accccgggtt cagaaaactg aaatcacaca cagtcagaca ctagccgtcc   2640
tcagccagaa acgagaaaaa aagcttcgcg gatccaattg atgatgagca tgtcaggcat   2700
tgattgtata aaatatccca cagggcagct tatcacccat ggaagagtga gtgcaaaaca   2760
taacgatggg aacctgaaag atagaagcga gaattctacc ccgggaacct gtgccctttc   2820
aggttgactg tatattgttc aaagaagtgg cagctgaatg catgaagagg tacattggca   2880
caccttatga gggaattgta agcttcgcgg atcctttcaa tatgctgaaa cgcgagagaa   2940
accgcgtgtc aactgtttca cagttggcga agagattctc aaaaggattg ctttcaggcc   3000
aaggacccat gaaattggtg atggctttta tagcgaattc taccccgggt tatgtgagga   3060
cacaatgacc tacaaatgcc cccggatcac tgagacggaa cctgaagaca ttgactgttg   3120
gtgcaatgaa gcttcgcgga tcc                                           3143

<210> SEQ ID NO 27
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gaattctacc ccggg                                                      15

<210> SEQ ID NO 28
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aagcttcgcg gatcc                                                      15
```

ARTIFICIAL CHIMERAS ENGINEERED TO SIMULATE MULTIPLE BIOLOGICAL THREAT AGENTS

RELATED APPLICATION

This application is a divisional of application Ser. No. 12/177,527, filed on Jul. 22, 2008, now U.S. Pat. No. 7,790,452.

FIELD OF THE INVENTION

This present invention includes the design and construction of non-infectious chimeras that include the nucleic acid signature of most bacterial and viral biological threat agents. One of the engineered chimeras simulates the biological threat agents whose genomes are DNA and the second engineered chimera simulates biological threat agents whose genomes are RNA. The chimeras of the present invention are also included in methods and devices of the present invention such as nucleic acid-based biodetectors and diagnostic products, and as simulants to allow the safe validation (and to compare) the performance of technologies, products, and devices used in biodefense, as well as in clinical detection and diagnosis of the said agents

BACKGROUND OF THE INVENTION

The threat of biological warfare has existed for centuries. By definition, biological warfare involves any deliberate use of disease to attack humans, plants, animals, or infrastructure. Biological weapons have been used only occasionally, but they have the potential to inflict great harm. Unlike the materials necessary to produce nuclear weapons, microorganisms, toxins, and viruses that are dangerous to human, animal, and plant life can be found abundantly in nature. The technology needed to turn these agents into weapons is less sophisticated than what is necessary to develop nuclear weapons. Furthermore, only a very small quantity of material is needed, much less than that needed to produce nuclear weapons, but could potentially cause a comparable death-toll.

Technology allows for some biological threat agents, which in their natural state pose only minimal dangers, to be genetically engineered into more threatening forms. Their availability in nature also changes, and science continues to discover new biological threat agents. The Center for Disease Control (CDC) and other agencies have compiled a list of the biological agents of greatest concern. They are segregated into categories, depending on a variety of factors.

Though the need to develop biological defense technologies to protect against the threat of terrorism is increasing, such biological defense technologies are hard to develop and test. Biological defense technologies are successful if they are able to detect the biological threat agent, inhibit biological threat agent contact with its host, inhibit biological threat agent growth, or kill the biological threat agent. Developing and testing biological defense technology in the presence of a biological threat agent poses serious hazards. Exposure of people working on defense technology, and/or the population at large, to a biological threat agent may result in serious Injury or death. Methods allowing the safe development, testing, and training of biological defense technology are needed to minimize, or eliminate, the potential hazards associated with such technology development. However, the use of actual virulent threat agents is costly and risky. Furthermore, development and testing of technologies dealing with more than one threat agent face almost insurmountable difficulties in producing, storing, and employing more than one threat agent simultaneously.

The use of biological threat agents in the development, testing, and training of biological defense technology is impaired by safety issues, high cost, the need of special infrastructure and uncommon expertise. A simulant is an agent having biological and/or physical characteristics similar to a biological threat agent but when used in place of the biological threat agent is not harmful. Though the use of methods involving simulants is a good idea, very few simulants have been identified and are being used. In biodefense a few simulants, including spores of *Bacillus subtilis* (as surrogate of *B. anthracis*), *Pantoea agglomerans* (as surrogate of all vegetative threat bacteria) and the phage M13 (as surrogate of all threat viruses), are used in methods development, training, and testing and evaluation of biodefense countermeasures, and equipment. These simulants are totally inadequate to simulate threat agents on nucleic-acid based technologies, since *B. subtilis*, *P. agglomerans*, and M13 do not share genes with any of the actual threat agents that they are intended to mimic

SUMMARY OF THE INVENTION

Accordingly, it is an object of the present invention to meet the foregoing needs by providing safe methods for the development, testing, and training of biological defense technology. One embodiment of the present invention is a chimera comprising a plurality of segments, wherein each segment uniquely corresponds to a portion of the genome of a threatening biological agent wherein the genome is DNA. It is preferred that the threatening biological agent is selected from the group consisting of: *Bacillus anthracis, Yersinia* species, *Burkholderia* species, *Francisella* species, *Brucella* species, *Coxiella burnetii, Ricketsia* species, enterohemorrhagic *Escherichia* species, and variola virus and the chimera further comprising a nucleic acid sequence comprising SEQ ID NO. 12. It is also preferred that the chimera of the present invention includes a segment having a DNA sequence derived from SEQ ID NOs: 1, 2, 3, 4, 5, 6, 7, 8, 9, 10, and 11.

Another embodiment of the present invention includes a chimera comprising a plurality of segments, wherein each segment uniquely corresponds to a portion of a genome of a threatening biological agent whose genome is RNA. It is preferred that the threatening biological agent is selected from the group consisting of: Eastern Equine Encephalitis Virus, Junin virus, Marburg virus, Dengue virus, Venezuelan Equine Encephalitis Virus, Crimean Congo virus, Influenza virus, Rift Valley Fever Virus, Machupo virus, Lassa virus, and Yellow Fever virus, and the chimera further comprising a nucleic acid sequence comprising SEQ ID NO. 26. It is also preferred that this chimera of the present invention includes segments of DNA sequences derived from SEQ ID NOs: 13, 14, 15, 16, 17, 18, 19, 20, 21, 22, 23, 24, and 25.

Another embodiment of the present invention includes a vector comprising a chimera of the present invention. The vector may be a plasmid, a virus, a cosmid, or a yeast artificial chromosome. Preferably the vector is a plasmid or a virus.

Another embodiment of the present invention includes a method of testing a detection technology, comprising the steps of: (a) providing a sample containing the chimera of the present invention in lieu of a sample containing a biological threat agent; and (b) using said detection technology in accordance with normal or standard procedures to detect threat agent in the sample; and (c) determining the effectiveness of said detection technology in detecting a portion of the chimera. It is preferred that the detection technology comprises a nucleic acid probe capable of selectively hybridizing to at least a portion of a chimera of the present invention. It is also preferred that this method of the present invention also comprises the step of measuring a level of detectable signal.

In yet another embodiment of the present invention, the chimeras of the present invention may be used as positive controls when conducting assays for detection of biological threat agents in samples. For example, if ten different samples suspected of containing threat agent were being tested to detect a biological threat agent, an eleventh sample containing a chimera of the present invention could be tested concurrently to ensure that a positive test result is obtained.

BRIEF DESCRIPTION OF THE DRAWINGS

The accompanying drawings, which are incorporated in and constitute a part of this specification, illustrate embodiments of the present invention and, together with the description, explain the advantages, and principles, of the Invention.

FIG. 1  Selection of Nucleic Acid Segments using Bioinformatics
FIG. 2  Design and Synthesis of Nucleic Acid Segments for Detecting Biological Threat Agents having DNA Genomes
FIG. 3  Design and Synthesis of Nucleic Acid Segments for Detecting Biological Threat Agents having RNA Genomes
FIG. 4  A Plasmid Containing the Chimera for Detecting Biological Threat Agents Having DNA Genomes.
FIG. 5  A Plasmid Containing the Chimera for Detecting Biological Threat Agents Having RNA Genomes
FIG. 6  Confirmation of simulant construct by release of biothreat-agent specific bands by restriction enzyme digestion and gel-electrophoresis analysis

DETAILED DESCRIPTION OF THE INVENTION

Figure 6:
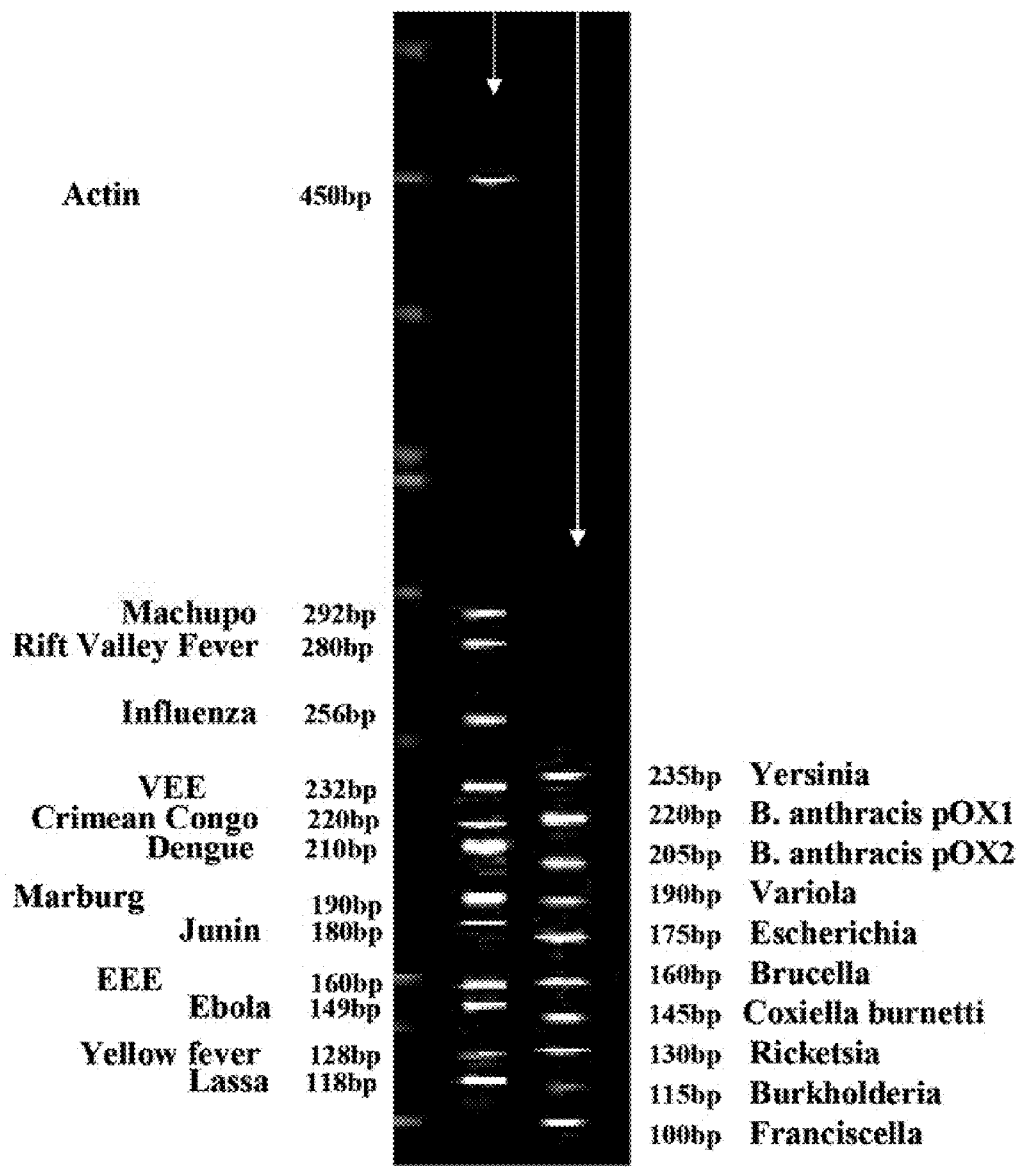

Reference will now be made to preferred embodiments of this invention. The current invention relates to biological threat agent simulants and to methods and products in which simulants replace biological threat agents during the development, testing, and/or training of biological defense technology. In order to better understand the invention, the following terms have been defined.

The term "biological defense technology" means a device, product and/or method able to detect a threatening biological agent, protect people, plants, livestock or other assets from contact with a threatening biological agent, and/or render harmless one or more threatening biological agents. Examples of biological defense technology include filters, masks, protective clothing, protective creams or gels, decontamination products and solutions, and devices or methods to detect and/or identify threat agents. A device includes a machine and/or equipment. A product includes a filter, gel, foam or other non-mechanical item. A method includes the use of a product and/or device.

The term "harmful" means resulting in injury, disease or death.

The term "inactivate" means to kill threat agent organisms, cells, spores or viruses and render them harmless or nonviable.

The term "virion" means a budded virus, or a virus not enmeshed in a polyhedrin matrix.

The term "simulant" means an agent having similar biological characteristics to a threatening biological agent but when used in place of the threatening biological agent is not harmful. The term includes one or more simulants and/or any combination of simulants.

The term "threatening biological agent" or "biological threat agent" means microorganisms, toxins, and/or viruses that are dangerous to human, animal, and/or plant life and as defined in this patent application. The term includes one or more threatening biological agents and/or any combination of threatening biological agents.

The term "virus threat agent" means a threatening biological agent that is a virus dangerous to human, animal, and/or plant life.

A simulant of the present invention is one or more agent(s), such as a nucleic acid sequence, preferably a DNA sequence that corresponds to one or more threatening biological agents. Such a simulant of the present invention takes the place of one or more threatening biological agents during the development, testing, and training of biological defense technologies.

Specifically, the simulant(s) of the present invention are chimeras; a genetic element made up of a plurality of nucleic acid segments, wherein each segment corresponds to the nucleic acid sequences of a threatening biological agent. The chimerical simulants are by design non-infectious to humans. Threatening biological agents are described within the Center for Disease Control (CDC) list of today's most dangerous biological agents, that is, within Category A, Category B, and/or Category C of the list. The CDC's list of the most dangerous biological agents includes organisms such as anthrax, plague, smallpox, tularemia, and viral hemorrhagic fevers.

The present invention specifically includes design and construction by genetic engineering of non-infectious chimeras that include the nucleic acid signature of most or all bacterial and viral biological threat agents. One embodiment of the present invention is chimeras that simulate biological threat agents whose genomes are DNA. Examples of biological threat agents whose genomes are DNA include: *Bacillus anthracis* (signatures from both virulent plasmids), *Yersinia* species, *Burkholderia species, Francisella species, Brucella species, Coxiella burnetii, Ricketsia* species, enterohemorrhagic *Escherichia* species, and variola virus (Smallpox). Another embodiment of the present invention is chimeras that simulate biological threat agents whose genome is RNA. Biological threat agents whose genome is RNA include members of the arenaviruses, filoviruses, alphaviruses, flaviviruses, and hantaviruses, more particularly the viruses: Ebola, Lassa, Yellow fever, Eastern Equine Encephalitis, Junin, Marburg, Dengue, Crimean-Congo, Venezuelean Equine Encephalitis, Rift Valley Fever, Machupo, and Influenza. The Chimeras once identified have been cloned into vectors such as viruses, plasmids or any other vehicle that allows the storage and amplification of the chimera sequences.

The risk of human injury or death is minimized when a simulant is used in the place of a threatening biological agent during the development, testing and/or training of a biological defense technology. Because the simulant and the threatening biological agent are selected to have similar characteristics (corresponding nucleic acid sequences) with the simulant being non-pathogenic, a simulant of the present invention may take the place of a threatening biological agent for product development, testing and evaluation, training, as positive controls, and wherever a non-infectious surrogate can beneficially replace actual threat agents. The results generated from such development, testing and/or training of a biological defense technology are then used to create new and effective biological defense technology, or improve existing biological defense technologies.

Discussion will now focus on examples of biological defense technology and their functions. Biological defense technology able to detect a threatening biological agent includes devices, products, and/or methods able to detect such agents in the air, in water, in food, in bodily fluids, or on solid surfaces. Detection of such agents in air generally consists of three steps: sample collection; sample processing; and sample analysis. Instrumentation accomplishing each step may be part of an integrated system, or samples may be collected, processed, and analyzed by separate systems (or by humans working with laboratory equipment). Some detection systems may sample the air passively, using currents in ambient air to cause airborne agents to move into the portion of the device that performs the analysis (in much the same way as a smoke detector detects smoke particles only when particle-laden air wafts into the interior of the detector).

Most active samplers that draw agents from air exploit one or more physical characteristics of the agents targeted for collection and contact with the biological defense technology. Such methods include but are not limited to the use of filters causing separation of particles from air based on size. Air can be drawn by fans (or other methods of moving air) and passed through filters designed with pore sizes small enough to retard the passage of airborne particles that carry virions. Another class of samplers accelerates air (and therefore airborne agents) and increases the momentum of airborne agents, then passes such particles through a path in the instrument in such a way that the momentum of particles causes them to leave the airstream and impact on a surface or into a fluid where they are arrested. Such devices are often said to work by "impaction" and may be called an "impaction sampler". Conceivably, air samplers for threatening biological agents could also work by adsorption (an adsorption sampler), in which air is passed through a column filled with a porous substrate that has an affinity for the threatening biological agents based on one or more methods, including but not limited to: charge, the complementarily of molecular surface structures (including but not limited to an antibody-antigen interaction), relative hydrophobicity/hydrophilicity. Sample collection from liquid samples employs many of the same techniques listed above.

Sample collection from surfaces usually employs the use of a swab (often composed of cotton, but can be any of a large number of materials) or other material or device that is wiped over a surface with the intent that particles on the surface adhere to the swab. Samples from food can involve the use of swabs or a more frequently a disruption of a portion of the food into a proper media and further analysis. Collection of samples from bodily fluids, including sputum, bronchial swabs or lavage, urine, feces, spinal fluid, or blood, is well known to those involved in the art.

The term "sample processing" refers to methods of preparing a sample for analysis, which is making the threatening biological agent or components thereof such as membrane proteins, DNA, and/or RNA accessible (able to come in contact with) to a detection device so that the detection device is able to detect the presence of a molecule characteristic to a biological threatening agent. Such molecules include RNA, DNA, protein and/or lipid (i.e., content and/or composition). Typically, the integrity of a threatening biological agent's cell, spore, or virion is disrupted by chemical, enzymatic, electrical, mechanical and/or other means. For example, such disruption means may cause the release of nucleic acids from a threatening biological agent and make them available for methods of analysis that rely upon nucleic acid sequence information for detection and identification. Another reason a sample might require preparation is that a molecule characteristic of a threatening biological agent may have to be modified or combined with other compounds before analysis. An example of this kind of modification is the derivatization of small molecules before gas chromatographic analysis.

A biological defense technology may detect a nucleic acid signature of a threatening biological agent. Nucleic acid hybridization is used to detect a biological agent by contacting a target nucleic acid (i.e. the nucleic acid signature specific to a particular threatening biological agent or simulant) with a nucleic acid probe capable of selectively hybridizing to at least a portion of the target nucleic acid sequence. The chimeras of the present invention are nucleic acid and can be detected by nucleic acid probes. Nucleic acid hybridization methods applicable to this invention are described in Sambrook et al. The detection may also occur by polymerase chain reaction (PCR) as described in Barlett et al.

PCR is typically used in nucleic acid based detection methods. Small amounts of biological threat agents may be present in a suspect sample and the corresponding low amount of nucleic acid sequences of the biological threat agents may have to be amplified to be detected. In order to amplify the nucleic acid sequences of a biological threat agent, lysis of the cell, or virus particle, preferably occurs by conventional methods. Then the nucleic acid sequences present in the sample are heated so that it becomes denatured to form single stranded nucleic acid sequences. The denatured nucleic acid sequences are cooled and nucleic acid probes are annealed. The probes are specific to the biological threat agent thought to be in the sample. Taq or equivalent polymerase binds the 3' end of each nucleic acid probe annealed to nucleic acid sequences and extends each of these primers in the 5' to 3' direction along the nucleic acid sequences. PCR typically results in a doubling of the number of copies of nucleic sequences after each round of DNA synthesis and a geometric increase in number of copies after each reaction cycle. The chimera in the present invention can be used to test different primers (probes), conditions, specificity, and sensitivity to be used in the PCR amplification method, or nucleic acid based detection methods. The PCR product (amplified nucleic acid sequence) can be observed afterwards by separation of the DNA by agarose gel electrophoresis, capillary electrophoresis, real time fluorescence, or other detection methods known to those familiar in the art.

Some biological defense technology must be able to detect very small amounts of threatening biological agents in a relative large amount of material; for example, a small number of anthrax spores in a thick layer of dust on top of a computer. Such non-pathogenic material collected with a threatening biological agent must be removed before a threatening biological agent may be detected and identified. Methods for the removal of such non-pathogenic materials may include, but are not limited to, purification by means of ligand-receptor affinity (of which antibody-antigen affinity or nucleic hybridization are possible examples).

Other types of decontamination technologies include but are not limited to methods and devices that transmit radiant energy (such as ultraviolet radiation) to threatening biological agent cells, spores, or virions in such a way that the absorbance of the radiant energy disrupts threatening biological agent cells, spores, or virions in the ways mentioned above. Another class of decontamination technology includes methods or devices that generate aerosols or gaseous emissions of substances that inactivate threatening biological agent cells, spores, or virions in the ways described above. An example of such a technology is a vaporous hydrogen peroxide (VHP) generator. Hydrogen peroxide vapors, chlorine dioxide, paraformaldehyde vapors, or combinations thereof, are capable of penetrating the interiors of equipment and destroying threatening biological agent cells by chemically (oxidatively or otherwise) modifying small or macromolecules of threatening biological agent cells, spores, or virions so that they are no longer viable or able to cause disease.

A simulant of the present invention is a chimera containing segments of nucleic acid sequences, which is safe when in contact with humans and is able to take the place of a biological threat agent, preferably during the development, testing, and training of biological defense technology.

EXAMPLES

Example 1

Design and Synthesis of a Nucleic Acid Segments for Detecting Biological Threat Agents Having DNA Genomes A single molecule chimera was made of DNA segments, each segment corresponding to the nucleic acid sequences of a biological threat agent having a DNA genome. The segments were identified using a novel bioinformatics approach. As shown in FIG. 1, this bioinformatics approach has multiple steps and uses computational tools to search and select non-infectious signature sequences corresponding to bacterial and viral threat agents whose genome is DNA, including *Bacillus anthracis, Yersinia pestis, Coxiella Burneti, Brucella* sp., *Francicella tularensis*, Entherohemorragic *E. coli*, O157: H7, *Burkholderia mallei, Burkholderia pseudomallei* and Variola virus (smallpox virus).

Once these nucleic acid sequences (or segments of the chimera) were identified, each segment was then prepared by PCR amplification. Synthetic chimeras were designed to produce PCR amplicons of different sizes than the amplified fragments from the original pathogenic genome (to identify any false positives).

Segments of the sizes shown in FIG. 2 were chosen to create the chimera for detecting Biological Threat Agents having DNA genomes. Added to each fragment were two restriction sites in the middle of the sequence (EcoRI -GAATTC- and SmaI -CCCGGG-). These enzymes won't cut the amplified segments from the microbial genomes; therefore the enzymes can be used to digest these segments in case of suspected contamination with the simulant. When the simulant amplicons were digested with internal restriction enzymes, two small fragments were obtained. (see right two columns in FIG. 2) For example, the *Francisella* tularensis simulant amplicon was a size of 100 bp and was digested by EcoR1 into two fragments of 37 bp and 63 bp were obtained. The corresponding fragment in the threat agent *Francisella* tularensis is 230 bp and is not digested by EcoR1.

Based on the bioinformatics study described in FIG. 1 and the primers (underlined in bold below) designed from segment sequences using the FastPCR software, DNA segments were selected as follows:

*Francisella* Segment

[SEQ ID NO. 1]

GGATCCGACAAGCTTATGGCTTTGCAGCCACTTTTGCAATCGCTGTGTGA

GCCCGGGCAGCGAATTCCCATTTAGATTTTTTTGAATATGCTTGTAAAGA

CCGAGGCTCAGAACTAATCGCAGCTACAGCACAAG

*Yersinia* Segment

[SEQ ID NUMBER: 2]

GGATCCTGAAAGCTTGCTGGGCGAACCCACCTCATTGGCTATGGCGGCGT

CGCCTGTCACGTCCTGTTTGAGTGGGATAAACGCCACGATGAGTTCGATCT

CGCCATACTGGAGAAAGCATGGAACCAGCTCATCGCACGCCACGATATGTT

GCGTATGGTGGTTGCCCGGGGCCTGAATTCTGACGATCCTCATTATGTCAA

TATCGGTACGGTGTTAGACAACGCCGACTGACGCCGGAGTATCACATCCCG

CGTGACGATCTGCGC

*Burkholderia* Segment

[SEQ ID NUMBER: 3]

GGATCCATGAAGCTTCATTCGTCTTTGCCATTGCCCTGTCATTTGCCGCA

GCCCGGGTGCTGAATTCGTCAGCAATGCGAAATTTACATCCCTACGCGAG

CCTTTTGTTTTTACCGACCTGAGTCTGTTCAGTCAGTTGTTCTCGCACCC pXO2 B. Anthracis Segment

[SEQ ID NUMBER: 4]

GGATCCCTCAAGCTTTTACACGTTTTGCTGACCAATCTAAGCCTGCGTTC

TTCGTAAATGGTTTTGCAGCGAATGATCCCTCATCAACATTACGTATTTG

GGAACGTGTGGATGATTTTGGATATAGTAATCTAGCTCCAATTGCCCGGG

AGATGAATTCTACATCTGCGCGAATGATATATTGGTTTACTGACGAGGAG

CAACCGATTAAGCGCCGTAGCGTTGATCGTACTGAGCAGTTTGCTAGGGA

TGTTT

*Rickettsia* Segment

[SEQ ID NUMBER: 5]

GGATCCGGAAAGCTTAGCTGGTATCGCTTATTTTAGAGGTTATAGAGTTC

GCCCGGGTAGTGAATTCGTAAACCTTTATTTTTTGATCTTAATATTTCTA

CTAGAACCCAAAACGTATCCCAAGTTCAAAGAGCTTTACTTTTACCTCAA

GAAGTAATACAGTTA pXO1 B. Anthracis Segment

[SEQ ID NUMBER: 6]

GGATCCTCTAAGCTTGAAAAAGGATTGGATTTCAAGTTGTACTGGACCGA

TTCTCAAAATAAAAAGAAGTGATTTCTAGTGATAACTTACAATTGCCAG

AATTAAAACAAAAATCTTCGAACTCAAGAAAACCCGGGGAAAGAATTCTC

ATCTCCTGAAAAATGGAGCACGGCTTCTGATCCGTACAGTGATTTCGAAA

AGGTTGGACCTACGGTTCCAGACCGTGACAATGATGGAAT

```
Coxiella Segment

[SEQ ID NUMBER: 7]

GGATCCACTAAGCTTCGGATTGTTACCCAACGAAACCTTGCGTGAGGCAT

TGAATCGGGAATTAGATGAAGAAGTGGGACTGAGTCCTCACCCGGGTAC

AGAATTCCAATGGCGGTGGGTTGATTATTGGTATCCGGTGGACCACGTCG

TTGAGTTTAAGCGAGACGTTTATCAGAAAGT

Variola Segment

[SEQ ID NUMBER: 8]

GGATCCATAAAGCTTCGGAAGAGATGCAGCACCGTATACACCACCCAATG

GAATCATTAGTATACTCTACACCTTATCCTCAGACACAGATATCTAAAAA

AATAGGTGATGATGCAACTCTATCATGTAGTAGAAATAATATACCCGGGA

CGTGAATTCCAAACAAAATGTGGAATAGGATACGGAGTATCCGGACACAC

GTCTGTTGGAGACGTCATCTGTTCT

Brucella Segment
[SEQ ID NUMBER: 9]
GGATCCTAGAAGCTTAATTGTGGGCCGATGGCGTCATCCATGTGCTGGGTG

TCGGGCTGGCGCTTGCCGGTGCCATTGCCATGCTGTTCTATTTCCTCCCGG

GAATCGAATTCTATGGGCGACCGCGCGCTGCCCCTGCTGCTGTTCGTGTGG

AGCGTGGCTTTCGTCGGCATCATGCTCAAACTGTTCATGCCG

Escherichia Segment

[SEQ ID NUMBER: 10]

GGATCCCTGAAGCTTGCGCGCTAACGCAGGCCTGAACTCATCGTCGGATG

AATTACAGGCCCAGACGCGTATTGCCGGAATGCGCTCAACGCTGGAGCAA

TATCACCCGGGGCACGAATTCAAGCGCAATACTGGCCAACGCTCAGTATT

CAGGGGGGTAAAACGCGCTACCAGACCAGCGACCGCTCGTATTGGGATGA

TCAGCTACAA

Smallpox Segment

[SEQ ID NUMBER: 11]

TCATTAGTATACTCTACACCTTATCCTCAGACACAGATATCTAAAAAAAT

AGGTGATGATGCAACTCTATCATGTAGTAGAAATAATATA
```

A chimera able to mimic many different types of biological threat agents was created by DNA synthesis and the joining of the above-identified segments. The whole chimera sequence for DNA genome threat agents is SEQ ID NUMBER: 12.

```
[SEQ ID NO: 12]

GGATCCGACAAGCTTATGGCTTTGCAGCCACTTTTGCAATCGCTGTGTGA

GCCCGGGCAGCGAATTCCCATTTAGATTTTTTTGAATATGCTTGTAAAGA

CCGAGGCTCAGAACTAATCGCAGCTACAGCACAAGGGATCCTGAAAGCTT

GCTGGGGCGAACCCACCTCATTGGCTATGGCGGCGTCGCCTGTCACGTCC

TGTTTGAGTGGGATAAACGCCACGATGAGTTCGATCTCGCCATACTGGAG

AAAGCATGGAACCAGCTCATCGCACGCCACGATATGTTGCGTATGGTGGT

TGCCCGGGGCCTGAATTCTGACGATCCTCATTATGTCAATATCGGTACGG

TGTTAGACAACGCCGACTGACGCCGGAGTATCACATCCCGCGTGACGATC

TGCGCGGATCCATGAAGCTTCATTCGTCTTTGCCATTGCCCTGTCATTTG

CCGCAGCCCGGGTGCTGAATTCGTCAGCAATGCGAAATTTACATCCCTAC

GCGAGCCTTTTGTTTTTACCGACCTGAGTCTGTTCAGTCAGTTGTTCTCG

CACCCGGATCCCTCAAGCTTTTACACGTTTTGCTGACCAATCTAAGCCTG

CGTTCTTCGTAAATGGTTTTGCAGCGAATGATCCCTCATCAACATTACGT

ATTTGGGAACGTGTGGATGATTTTGGATATAGTAATCTAGCTCCAATTGC

CCGGGAGATGAATTCTACATCTGCGCGAATGATATATTGGTTTACTGACG

AGGAGCAACCGATTAAGCGCCGTAGCGTTGATCGTACTGACCAGTTTGCT

AGGGATGTTTGGATCCGGAAAGCTTAGCTGGTATCGCTTATTTTAGAGGT

TATAGAGTTCGCCCGGGTAGTGAATTCGTAAACCTTTATTTTTTGATCTT

AATATTTCTACTAGAACCCAAAACGTATCCCAAGTTCAAAGAGCTTTACT

TTTACCTCAAGAAGTAATACAGTTAGGATCCTCTAAGCTTGAAAAAGGAT

TGGATTTCAAGTTGTACTGGACCGATTCTCAAAATAAAAAAGAAGTGATT

TCTAGTGATAACTTACAATTGCCAGAATTAAAACAAAAATCTTCGAACTC

AAGAAAACCCGGGGAAAGAATTCTCATCTCCTGAAAAATGGAGCACGGCT

TCTGATCCGTACAGTGATTTCGAAAAGGTTGGACCTACGGTTCCAGACCG

TGACAATGATGGAATGGATCCACTAAGCTTCGGATTGTTACCCAACGAAA

CCTTGCGTGAGGCATTGAATCGGGAATTAGATGAAGAAGTGGGACTGAGT

CCTCACCCGGGTACAGAATTCCAATGGCGGTGGGTTGATTATTGGTATCC

GGTGGACCACGTCGTTGAGTTTAAGCGAGACGTTTATCAGAAAGTGGATC

CATAAAGCTTCGGAAGAGATGCAGCACCGTATACACCACCCAATGGAATC

ATTAGTATACTCTACACCTTATCCTCAGACACAGATATCTAAAAAAATAG

GTGATGATGCAACTCTATCATGTAGTAGAAATAATATACCCGGGACGTGA

ATTCCAAACAAAATGTGGAATAGGATACGGAGTATCCGGACACACGTCTG

TTGGAGACGTCATCTGTTCTGGATCCTAGAAGCTTAATTGTGGGCCGATG

GCGTCATCCATGTGCTGGGTGTCGGGCTGGCGCTTGCCGGTGCCATTGCC

ATGCTGTTCTATTTCCTCCCGGGAATCGAATTCTATGGGCGACCGCGCGC

TGCCCCTGCTGCTGTTCGTGTGGAGCGTGGCTTTCGTCGGCATCATGCTC

AAACTGTTCATGCCGGGATCCCTGAAGCTTGCGCGCTAACGCAGGCCTGA

ACTCATCGTCGGATGAATTACAGGCCCAGACGCGTATTGCCGGAATGCGC
```

-continued

TCAACGCTGGAGCAATATCACCCGGGGCACGAATTCAAGCGCAATACTGG

CCAACGCTCAGTATTCAGGGGGGTAAAACGCGCTACCAGACCAGCGACCG
CTCGTATTGGGATGATCAGCTACAAAAGCTTAGAGGATCC

Figure 4:
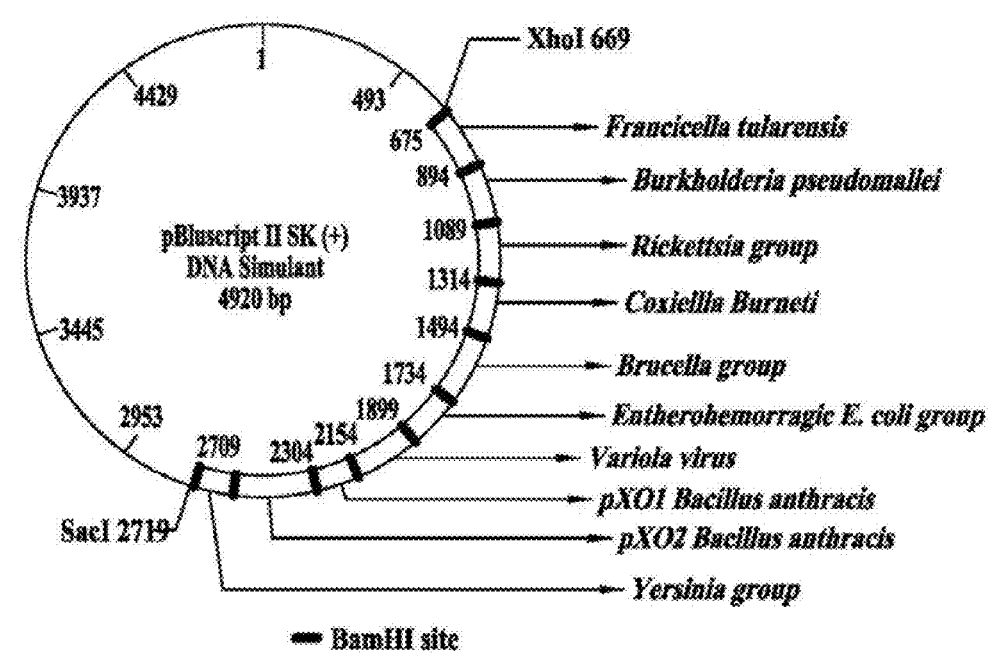

A plasmid map comprising the whole chimera is shown in FIG. 4.

Example 2

Design and Synthesis of a Nucleic Acid Segments for Detecting Biological Threat Agents Having RNA Genomes The strategy used to identify nucleic acid segments unique to Biological Threat Agents was different than that used in Example 1. The reason is that there is a higher probability of finding a unique DNA in larger bacterial genomes (Example 1) than in smaller viral genomes due to the significant disparity in genomic size between bacteria and viruses. Smaller viral genomes (Example 2) have been sequenced completely, unlike bacterial genomes requiring the need of large sequencing efforts. To obtain segments, or conserved regions of nucleic acid, among all isolates of one viral species, the genome sequences from all available isolates were aligned using ClustalW software (Thompson, J. D. et al 1997). The selection of possible primer sequences was performed manually looking at the alignments. This analytical approach was used to determine target nuclei acid sequence representing several RNA virus whose genome is RNA, Including but not limited to, nucleic acids in VEEV (Venezuelan Equine Encephalitis Virus), Influenza virus, Rift Valley Fever Virus, Machupo virus, Lassa virus, Yellow Fever virus, Ebola Zaire virus, Eastern Equine Encephalitis Virus, Junin virus, Marburg virus, Dengue virus, Crimean Congo virus.

Primer sequences were then selected manually by looking at the sequence alignments. Then Fast PCR was used as described in Example 1.

The following DNA Sequences were selected, based on the manual selection described above, and primers (underlined in sequences below) were designed from segment sequences using the FastPCR software for purposes of designing and chemically synthesizing the whole chimera as follows:

Restriction Sites:

GAATTCTACCCCGGG EcoRI/SmaI (intrafragments sites)

AAGCTTCGCGGATCC HindIII/BamHI (interfragments-sites)

Ebola Segment

[SEQ ID NUMBER: 13]

AAGCTTCGCGGATCCCGGCAATTGCACTCGGAGTCGCCACAGCACACGGG

AGTACCCTCGCAGGAGTAAATGTTGGAGAACAGTATCAACAACTCAGAGA

GGCTGCCACTGAGGCTGAGAAGCAAGAATTCTACCCCGGGTGCTGCGTCA

CTGCCCAAAACAAGTGGA

EEEV Segment

[SEQ ID NUMBER: 14]

AAGCTTCGCGGATCCTTTACTTGTCTGCGGCGCCTTGGGCGCCGTAGTCGA

ACGCCCAGGTTATGCACCCGTTCACCTACAGATACAGCTGGTTAATACCAG

GATAATTCCATCAAGAATTCTACCCCGGGACAGGTGTTTACCCATTCATCT

GGGGAGGAGCCTACTGCTTCTGCGAC

Junin Segment

[SEQ ID NUMBER: 15]

AAGCTTCGCGGATCCGCACCTCTGATCCAGACATGCAGTCGACCCTTAACT

TGACATCAAATCCACATGATGGATTTGATTTGCATATGCCATCAAGAAAT

ATCTTAGACCTTGTAAAAATGTCTGGTTCCGAATTCTACCCCGGGCCCATT

GATGGATAGATAGATAGAATAGCACCTTGACTTCTCACCTGTTTTT

Marburg Segment

[SEQ ID NUMBER: 16]

AAGCTTCGCGGATCCATGAAGTTGCTAGTTTCAAGCAGGCGTTGAGCAACC

TAGCCCGACATGGAGAATACGCACCGTTCGCACGGGTTCTGAATTTATCAG

GGATTAACAACCTCGAACATGGACTCTATCGAATTCTACCCCGGGTTCAGA

AAACTGAAATCACACACAGTCAGACACTAGCCGTCCTCAGCCAGAAACGAG

AAAAAA

Dengue Segment

[SEQ ID NUMBER: 17]

AAGCTTCGCGGATCCTTTCAATATGCTGAAACGCGAGAGAAACCGCGTGTC

AACTGTTTCACAGTTGGCGAAGAGATTCTCAAAAGGATTGCTTTCAGGCCA

AGGACCCATGAAATTGGTGATGGCTTTTATAGCGAATTCTACCCCGGGTTA

TGTGAGGACACAATGACCTACAAATGCCCCCGGATCACTGAGACGGAACCT

GAAGACATTGACTGTTGGTGCAATG

VEEV Segment

[SEQ ID NUMBER: 18]

AAGCTTCGCGGATCCTAGTTAGTTGCGACGGGTACGTCGTTAAAAGAATAG

CTATCAGTCCAGGCCTGTATGGGAAGCCTTCAGGCTATGCTGCTACGATGC

ACCGTTAAAAGAATAGCTATCAGGAATTCTACCCCGGGGCTATGCTGCTA

CGATGCACCGTTAAAAGAATAGCTATCAGTCCAGGCCTGTATGGGAAGCCT

TCAGGCTATGCTGCTACGATGCACCGCGAGGGATTCTTGTGCTGCAA

Crimean Congo Segment

[SEQ ID NUMBER: 19]

AAGCTTCGCGGATCCAATTGATGATGAGCATGTCAGGCATTGATTGTATAA

AATATCCCACAGGGCAGCTTATCACCCATGGAAGAGTGAGTGCAAAACATA

ACGATGGGAACCTGAAAGATAGAAGCGAGAATTCTACCCCGGGAACCTGTG

CCCTTTCAGGTTGACTGTATATTGTTCAAAGAAGTGGCAGCTGAATGCATG

AAGAGGTACATTGGCACACCTTATGAGGGAATTGT

Influenza Segment

[SEQ ID NUMBER: 20]

AAGCTTCGCGGATCCAAACCATTTGAATGGATGTCAATCCGACTCTACTGT

TCCTAAAGGTTCCAGCGCAAAATGCCATAAGCACCACATTCCCTTATACTG

GAGATCCTCCATACAGCCATGGAACAGTCTACTGTTGAATTCTACCCCGGG

TGGAACAGTCTACTGTTCCTAAAGGTTCCAGCGCAAAATGCCATAAGCACC

ACATTCCCTTATACTGGAGATCCTCCATACAGCCATGGAACAGGAACAGGA

TACACCATGGACACAGTCAA

RVFV Segment

[SEQ ID NUMBER: 21]

AAGCTTCGCGGATCCTTATGAGTGCACTGCTCAGTACGCCAATGCCTATTG

TTCACATGCTAATGGGTCAGGGATTGTGCAGATACAAGTATCAGGGGTCTG

GAAGAAGCCTTTATGTGTAGGGTATGAGAGAGTGGTTGTGAAGAGAGGAAT

TCTACCCCGGGACATGCTAATGGGTCAGGGATTGTGCAGATACAAGTATCA

GGGGTCTGGAAGAAGCCTTTATGTGTAGGGTATGAGAGAGTGGTTGTGAAG

AGAGAACTCTCTGCCAAGCCCATCCAGAGAGTTGAGCCTTGCAC

Machupo Segment

[SEQ ID NUMBER: 22]

AAGCTTCGCGGATCCTTCATTCATCATGTCTAAAGCAATGCAGACATCCAG

AAATTTTAGCCTCCCGCTATCCATTGTTCTGCTGACCTGAAGATCATTCAT

AAATGGAGTCAAGTGTTCGTCAAAAAGAACTGGATAATTTCTCCTTATAGA

TTGAATTCTACCCCGGGTCTGCTGACCTGAAGATCATTCATAAATGGAGTC

AAGTGTTCGTCAAAAAGAACTGGATAATTTCTCCTTATAGATTGCAGAACA

TGGTTCATTCCCAGTTGGTCTTCAATTTGTCTCACCACTTTAGGCTTCACA

GCCCA

Lassa Segment

[SEQ ID NUMBER: 23]

AAGCTTCGCGGATCCTTATCCTGGGTGACCACTTCATTTTGGTTGATGCTA

AGTCGCTCATAAATGGCAGTATGTGTTTTTCAAATACAGATGGGAATTCTA

CCCCGGGAAGACCCATGCACCCAGTTCTATTGCAG

Yellow Fever Segment

[SEQ ID NUMBER: 24]

AAGCTTCGCGGATCCTGCTAAGCTGTGAGGCAGTGCAGGCTGGGACAGCCG

ACCTCCAGGTTGCGAAAAACCTGGTTTCTGGGACCTCCCACCCCAGAGTAA

AAGAATTCTACCCCGGGCAGTTTGCTCAAGAATAAGCAGACCTTT

Actin Segment (450pb)

[SEQ ID NUMBER: 25]

AAGCTTCGCGGATCCGCGTCCGCCCCGCGAGCACAGAGCCTCGCCTTTGCC

GATCCGCCGCCCGTCCACACCCGCCGCCAGCTCACCATGGATGATGATATC

GCCGCGCTCGTCGTCGACAACGGCTCCGGCATGTGCAAGGCCGGCTTCGCG

GGCGACGATGCCCCCCGGGCCGTCTTCCCCTCCATCGTGGGGCGCCCCAGG

CACCAGGGCGTGATGGTGGGCATGGGTCAGAAGGATTCCGAATTCTACCCC

GGGTATGTGGGCGACGAGGCCCAGAGCAAGAGAGGCATCCTCACCCTGAAG

TACCCCATCGAGCACGGCATCGTCACCAACTGGGACGACATGGAGAAAATC

TGGCACCACACCTTCTACAATGAGCTGCGTGTGGCTCCCGAGGAGCACCCC

GTGCTGCTGACCGAGGCCCCCCTGAACCCCAAGGCCAACCGCGAGAAGATG

ACCCAGATCATGTTTGAGACCTTCAA

These segments were then joined together to form a chimera to mimic many different types of biological threat agents whose genome is RNA. DNA synthesis was used to create the whole chimera based on the joining of segments. The entire chimera sequence for threat agents having RNA genomes is SEQ ID NO: 26.

[SEQ ID NUMBER: 26]

AAGCTTCGCGGATCCTTATCCTGGGTGACCACTTCATTTTGGTTGATGCTA

AGTCGCTCATAAATGGCAGTATGTGTTTTTCAAATACAGATGGGAATTCTA

CCCCGGGAAGACCCATGCACCCAGTTCTATTGCAGAAGCTTCGCGGATCCG

CGTCCGCCCCGCGAGCACAGAGCCTCGCCTTTGCCGATCCGCCGCCCGTCC

ACACCCGCCGCCAGCTCACCATGGATGATGATATCGCCGCGCTCGTCGTCG

ACAACGGCTCCGGCATGTGCAAGGCCGGCTTCGCGGGCGACGATGCCCCCC

GGGCCGTCTTCCCCTCCATCGTGGGGCGCCCCAGGCACCAGGGCGTGATGG

TGGGCATGGGTCAGAAGGATTCCGAATTCTACCCCGGGTATGTGGGCGACG

AGGCCCAGAGCAAGAGAGGCATCCTCACCCTGAAGTACCCCATCGAGCACG

GCATCGTCACCAACTGGGACGACATGGAGAAAATCTGGCACCACACCTTCT

ACAATGAGCTGCGTGTGGCTCCCGAGGAGCACCCCGTGCTGCTGACCGAGG

CCCCCCTGAACCCCAAGGCCAACCGCGAGAAGATGACCCAGATCATGTTTG

AGACCTTCAAAAGCTTCGCGGATCCTGCTAAGCTGTGAGGCAGTGCAGGCT

GGGACAGCCGACCTCCAGGTTGCGAAAAACCTGGTTTCTGGGACCTCCCAC

CCCAGAGTAAAAGAATTCTACCCCGGGCAGTTTGCTCAAGAATAAGCAGAC

CTTAAGCTTCGCGGATCCTTCATTCATCATGTCTAAAGCAATGCAGACAT

CCAGAAATTTTAGCCTCCCGCTATCCATTGTTCTGCTGACCTGAAGATCAT

-continued

```
TCATAAATGGAGTCAAGTGTTCGTCAAAAAGAACTGGATAATTTCTCCTTA
TAGATTGAATTCTACCCCGGGTCTGCTGACCTGAAGATCATTCATAAATGG
AGTCAAGTGTTCGTCAAAAAGAACTGGATAATTTCTCCTTATAGATTGCAG
AACATGGTTCATTCCCAGTTGGTCTTCAATTTGTCTCACCACTTTAGGCTT
CACAGCCCAAAGCTTCGCGGATCCCGGCAATTGCACTCGGAGTCGCCACAG
CACACGGGAGTACCCTCGCAGGAGTAAATGTTGGAGAACAGTATCAACAAC
TCAGAGAGGCTGCCACTGAGGCTGAGAAGCAAGAATTCTACCCCGGGTGCT
GCGTCACTGCCCAAAACAAGTGGAAAGCTTCGCGGATCCTTATGAGTGCAC
TGCTCAGTACGCCAATGCCTATTGTTCACATGCTAATGGGTCAGGGATTGT
GCAGATACAAGTATCAGGGGTCTGGAAGAAGCCTTTATGTGTAGGGTATGA
GAGAGTGGTTGTGAAGAGAGGAATTCTACCCCGGGACATGCTAATGGGTCA
GGGATTGTGCAGATACAAGTATCAGGGGTCTGGAAGAAGCCTTTATGTGTA
GGGTATGAGAGAGTGGTTGTGAAGAGAGAACTCTCTGCCAAGCCCATCCAG
AGAGTTGAGCCTTGCACAAGCTTCGCGGATCCTTTACTTGTCTGCGGCGCC
TTGGGCGCCGTAGTCGAACGCCCAGGTTATGCACCCGTTCACCTACAGATA
CAGCTGGTTAATACCAGGATAATTCCATCAAGAATTCTACCCCGGGACAGG
TGTTTACCCATTCATGTGGGAGGAGCCTACTGCTTCTGCGACAAGCTTCG
CGGATCCAAACCATTTGAATGGATGTCAATCCGACTCTACTGTTCCTAAAG
GTTCCAGCGCAAAATGCCATAAGCACCACATTCCCTTATACTGGAGATCCT
CCATACAGCCATGGAACAGTCTACTGTTGAATTCTACCCCGGGTGGAACAG
TCTACTGTTCCTAAAGGTTCCAGCGCAAAATGCCATAAGCACCACATTCCC
TTATACTGGAGATCCTCCATACAGCCATGGAACAGGAACAGGATACACCAT
GGACACAGTCAAAAGCTTCGCGGATCCGCACCTCTGATCCAGACATGCAGT
CGACCCTTAACTTTGACATCAAATCCACATGATGGATTTGATTTGCATATG
CCATCAAGAAATATCTTAGACCTTGTAAAAATGTCTGGTTCCGAATTCTAC
CCCGGGCCCATTGATGGATAGATAGATAGAATAGCACCTTGACTTCTCACC
TGTTTTTAAGCTTCGCGGATCCTAGTTAGTTGCGACGGGTACGTCGTTAAA
AGAATAGCTATCAGTCCAGGCCTGTATGGGAAGCCTTCAGGCTATGCTGCT
ACGATGCACCGTTAAAAGAATAGCTATCAGGAATTCTACCCCGGGGCTAT
GCTGCTACGATGCACCGTTAAAAGAATAGCTATCAGTCCAGGCCTGTATGG
GAAGCCTTCAGGCTATGCTGCTACGATGCACCGCGAGGGATTCTTGTGCTG
CAAAAGCTTCGCGGATCCATGAAGTTGCTAGTTTCAAGCAGGCGTTGAGCA
ACCTAGCCCGACATGGAGAATACGCACCGTTCGCACGGGTTCTGAATTTAT
CAGGGATTAACAACCTCGAACATGGACTCTATCGAATTCTACCCCGGGTTC
AGAAAACTGAAATCACACACAGTCAGACACTAGCCGTCCTCAGCCAGAAAC
GAGAAAAAAAGCTTCGCGGATCCAATTGATGATGAGCATGTCAGGCATTGA
TTGTATAAAATATCCCACAGGGCAGCTTATCACCCATGGAAGAGTGAGTGC
AAAACATAACGATGGGAACCTGAAAGATAGAAGCGAGAATTCTACCCCGGG
AACCTGTGCCCTTTCAGGTTGACTGTATATTGTTCAAAGAAGTGGCAGCTG
AATGCATGAAGAGGTACATTGGCACACCTTATGAGGGAATTGTAAGCTTCG
CGGATCCTTTTCAATATGCTGAAACGCGAGAGAAACCGCGTGTCAACTGTTT
CACAGTTGGCGAAGAGATTCTCAAAAGGATTGCTTTCAGGCCAAGGACCCA
TGAAATTGGTGATGGCTTTTATAGCGAATTCTACCCCGGGTTATGTGAGGA
CACAATGACCTACAAATGCCCCCGGATCACTGAGACGGAACCTGAAGACAT
TGACTGTTGGTGCAATGAAGCTTCGCGGATCC

Size: 3143 by
```

Once these nucleic acid sequences (or segments of the chimera) were identified, each segment was then prepared by PCR amplification. Synthetic chimeras were designed to produce PCR amplicons of different sizes (as indicated in FIG. 3) than the amplified fragments from the original pathogenic genome (to prevent that any contamination with simulant could create false positives).

Figure 5:
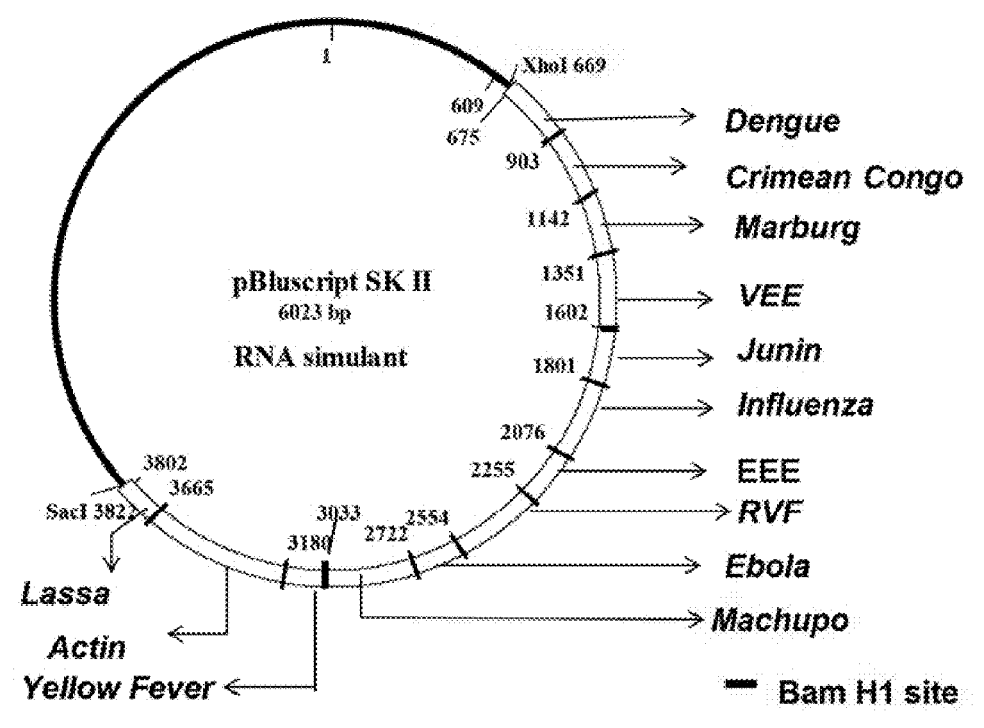

The chimera containing sequences corresponding to Biological Threat Agents having RNA genomes was inserted in the plasmid vector pBluscript SKII. A plasmid drawing comprising the whole chimera is described in FIG. 5, that shows the location in the plasmid vector of segments specific to each biothreat agent (separated by a Barn H1 restriction site), as well as the positions of restriction enzymes (Sad and XhoI) at the extremes of the insert.

The correct design and construction of the chimerical simulants (one for DNA agents and the other for RNA agents) was experimentally confirmed by releasing the inserts from the plasmid vector by digestion with one of the intersegment restriction enzymes (BamH1), performing multiplex PCR (using as primers the oligonucleotides underlined in sequences 1-26), and subsequent electrophoretic analysis shown in FIG. 6. The two vertical columns pointed by arrows in the gel in FIG. 6 correspond to nucleic acid fragments of the expected size (as indicated in FIG. 3) for agents whose genome is RNA (bands in column pointed by short downward arrow), and nucleic acids of the expected size (as indicated in FIG. 2) for agents whose genome is DNA (bands in column pointed by long downward arrow). The names of the agents are aligned to the corresponding fragments and their sizes are indicated (in base pairs, bp) at each side of the image representing the gel electrophoresis analysis.

REFERENCES

Sambrook, J., E. F. Fritsch, and T. Maniatis. 1989. Molecular Cloning: a Laboratory Manual, 2nd ed. Cold Spring Harbor Laboratory Press, Cold Spring Harbor, N.Y.

Bartlett J. M. S., Stirling D., eds. 2003. PCR Protocols, $2^{nd}$ ed. (Volume 226 in the series Methods in Molecular Biology.) Humana Press, Totowa, N.J.

Thompson J. D., Gibson T. J., Plewniak F., Jeanmougin F., and Higgins D.G. The CLUSTAL_X windows interface: flexible strategies for multiple sequence alignment by quality analysis tools. Nucleic Acids Res. 1997 Dec. 15; 25(24): 4876-82.

The foregoing description of embodiments of the present invention provides an exemplary illustration and description, but is not intended to be exhaustive or to limit the invention to the precise form disclosed. Modifications and variations are possible in light of the above teachings or may be acquired from practice of the invention.

What is claimed is:

1. A method of detecting a biological threat agent, comprising the steps of:

(a) providing one or more samples suspected of containing one or more biological threat agents;

(b) performing a nucleic-acid based detection method to detect said one or more biological threat agents in said one or more samples;

(c) providing an additional sample containing a chimera comprising a plurality of segments, wherein each segment uniquely corresponds to a portion of the genome of a biological threat agent whose genome is DNA, and wherein said plurality of segments comprises a nucleic acid sequence comprising SEQ ID NO: 12; and (d) performing said nucleic-acid based detection method to detect said chimera in said additional sample as a positive control.

2. The method of claim 1, wherein the detection method comprises one or more nucleic acid probe methods.

3. The method of claim 1, wherein the detection method comprises PCR amplification methods.

* * * * *